US012114902B2

(12) United States Patent
Biedermann et al.

(10) Patent No.: US 12,114,902 B2
(45) Date of Patent: Oct. 15, 2024

(54) INSTRUMENT FOR USE WITH A BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Achim Schünemann, VS-Mühlhausen (DE); René Zandomeni, Vohrenbach (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 651 days.

(21) Appl. No.: 17/124,975

(22) Filed: Dec. 17, 2020

(65) Prior Publication Data

US 2021/0186575 A1 Jun. 24, 2021

Related U.S. Application Data

(60) Provisional application No. 62/949,877, filed on Dec. 18, 2019.

(30) Foreign Application Priority Data

Dec. 18, 2019 (EP) ..................................... 19217722

(51) Int. Cl.
*A61B 17/70* (2006.01)
*A61B 17/56* (2006.01)
(52) U.S. Cl.
CPC ...... *A61B 17/7076* (2013.01); *A61B 17/7032* (2013.01); *A61B 2017/564* (2013.01)

(58) Field of Classification Search
CPC ............ A61B 17/7076; A61B 17/7091; A61B 17/708; A61B 17/7079
See application file for complete search history.

(56) References Cited

U.S. PATENT DOCUMENTS 10,349,986 B2* 7/2019 Wall .................... A61B 17/7032
2006/0293666 A1 12/2006 Matthis et al.
(Continued)

FOREIGN PATENT DOCUMENTS

WO 2020/023259 A1 1/2020

OTHER PUBLICATIONS

Extended European Search Report for Application No. 19217722.8, mailed Jun. 23, 2020, 10 pages.

*Primary Examiner* — Julianna N Harvey
(74) *Attorney, Agent, or Firm* — Lewis Roca Rothgerber Christie LLP

(57) ABSTRACT

An instrument is configured for use with a receiving part defining a recess for receiving a rod to connect the rod to a bone anchoring element. The instrument includes a tube having a first end and a second end, and defining a coaxial internal channel that opens towards the first and second ends, and at least one protruding portion monolithically formed with the tube that is engageable with the recess of the receiving part to prevent rotational movement of the tube relative to the receiving part. The first end of the tube forms a closed ring. The at least one protruding portion has a first region that extends radially outwardly from an outer surface of the tube at the first end and a second region that extends axially away from the first end in a direction opposite the second end.

20 Claims, 14 Drawing Sheets

(56) References Cited

U.S. PATENT DOCUMENTS

| | | | |
|---|---|---|---|
| 2008/0125789 A1* | 5/2008 | Butters | A61B 17/7077 |
| | | | 606/105 |
| 2010/0114174 A1 | 5/2010 | Jones et al. | |
| 2011/0077690 A1* | 3/2011 | Shin | A61B 17/7085 |
| | | | 606/86 R |
| 2012/0123431 A1* | 5/2012 | Robinson | A61B 17/808 |
| | | | 606/104 |
| 2012/0191144 A1* | 7/2012 | Peultier | A61B 17/7086 |
| | | | 606/279 |
| 2014/0100616 A1* | 4/2014 | Shipp | A61B 17/7082 |
| | | | 606/86 A |
| 2014/0163625 A1* | 6/2014 | Meyer | A61B 17/7085 |
| | | | 606/86 A |
| 2015/0051648 A1 | 2/2015 | May et al. | |
| 2015/0148849 A1* | 5/2015 | Abidin | A61B 17/7091 |
| | | | 606/279 |
| 2015/0257798 A1* | 9/2015 | Biedermann | A61B 17/7082 |
| | | | 606/86 A |
| 2017/0348029 A1* | 12/2017 | Asaad | A61B 17/7032 |
| 2018/0353223 A1* | 12/2018 | Otsubo | A61B 17/7082 |

\* cited by examiner

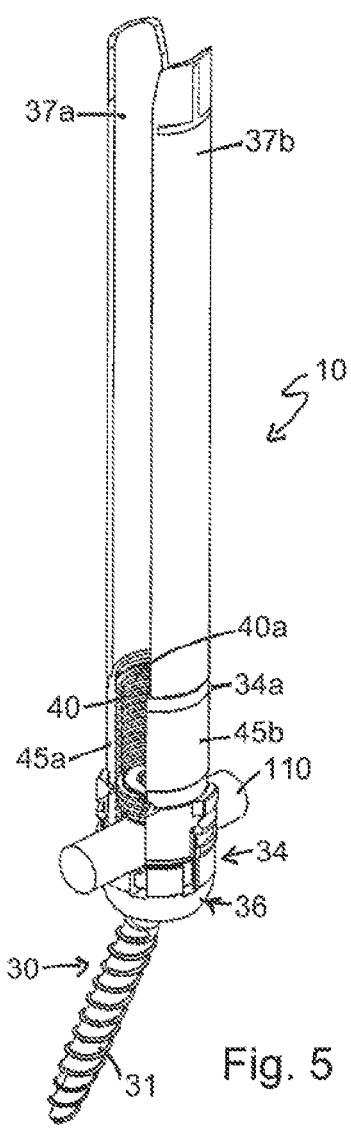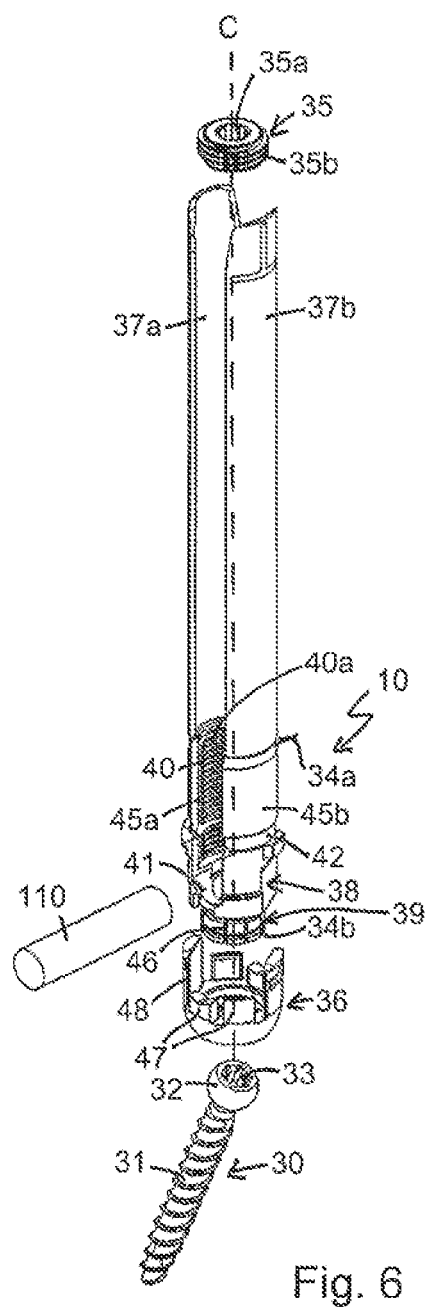
Fig. 5
Fig. 6

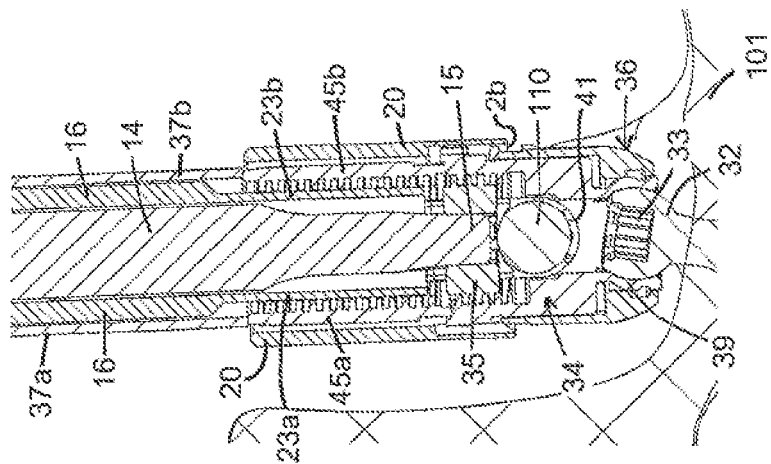
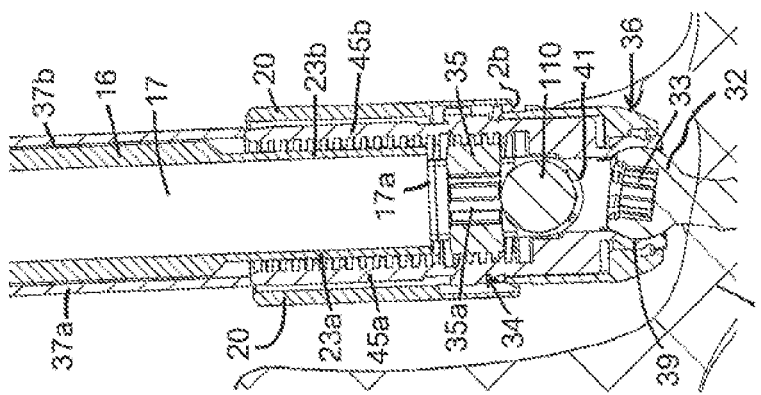
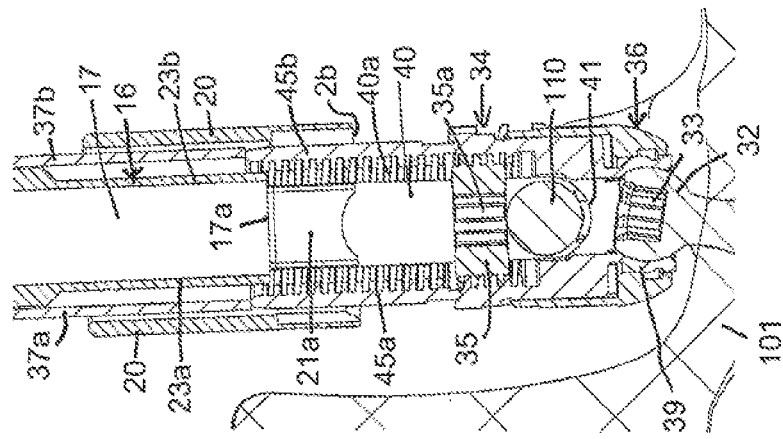

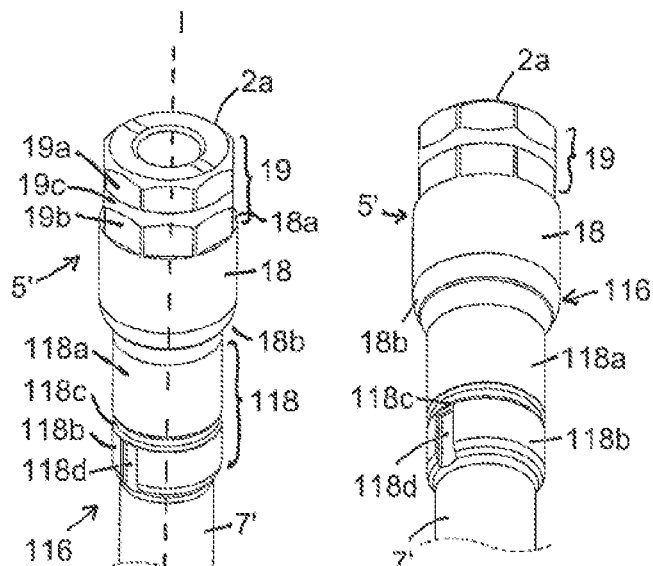
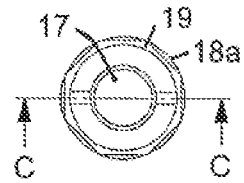
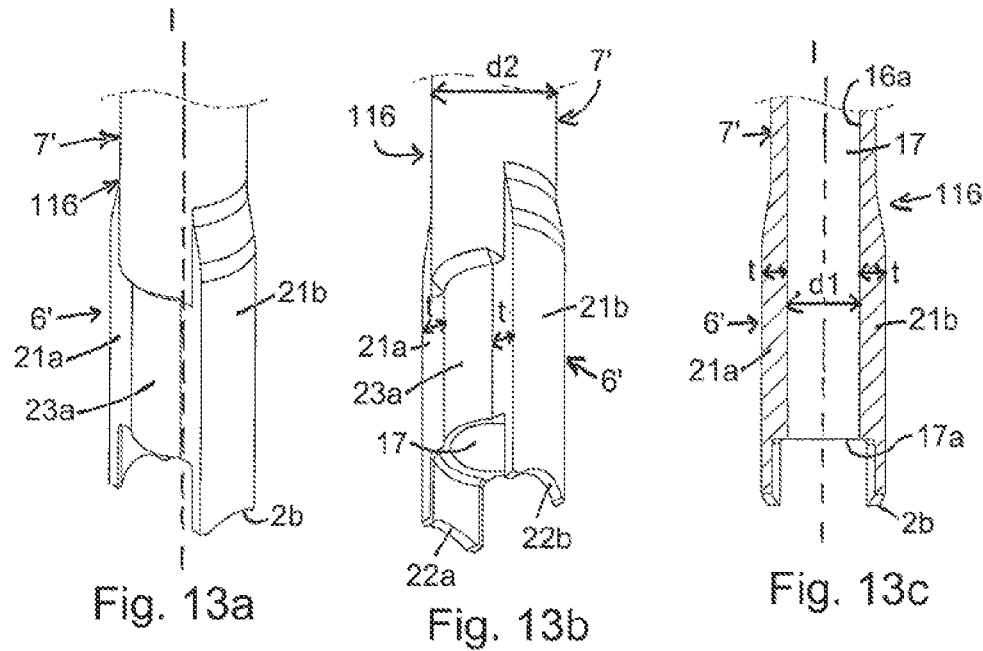

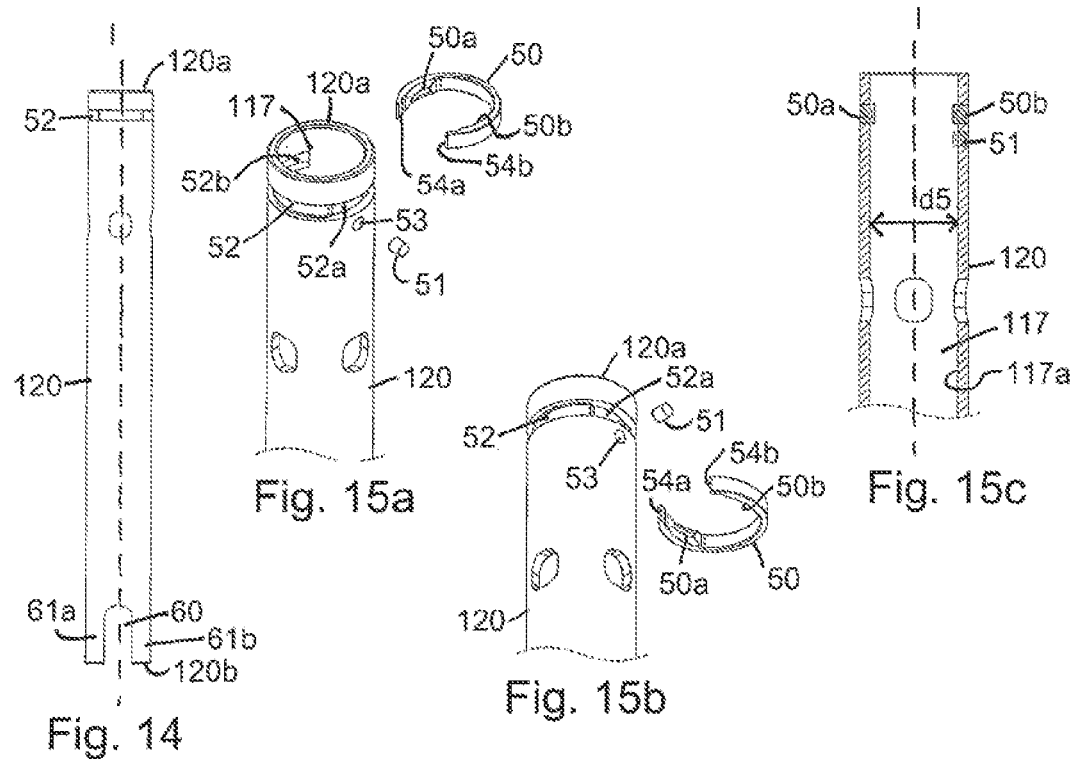
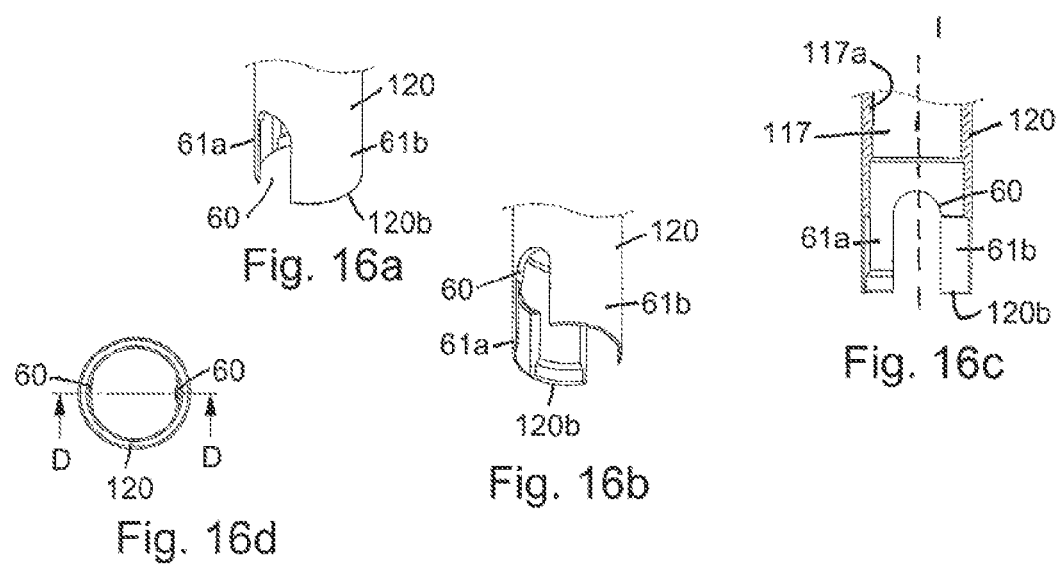

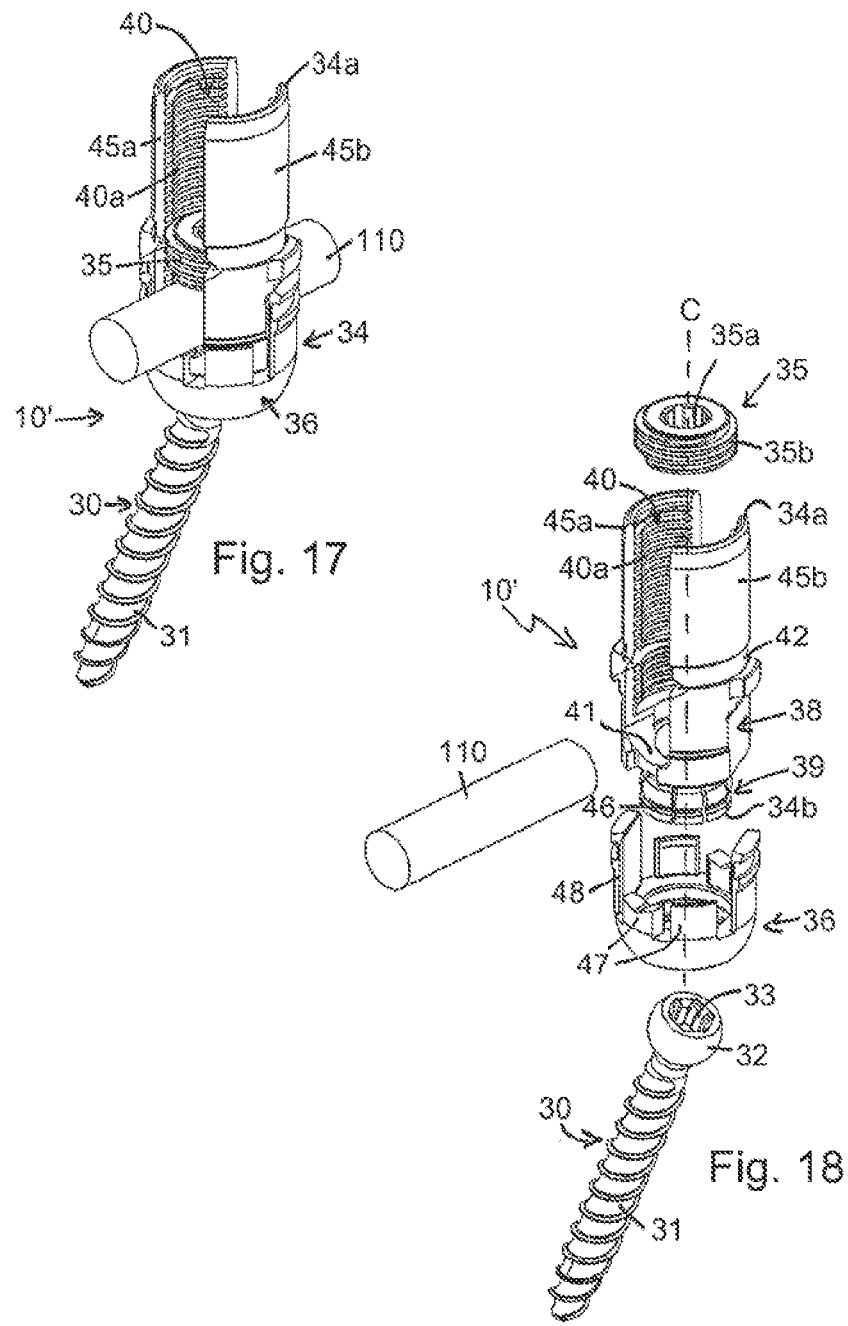

INSTRUMENT FOR USE WITH A BONE ANCHORING DEVICE

CROSS-REFERENCE TO RELATED APPLICATION(S)

The present application claims priority to and the benefit of U.S. Provisional Patent Application No. 62/949,877, filed Dec. 18, 2019, the contents of which are hereby incorporated by reference in their entirety, and claims priority from European Patent Application EP 19 217 722.8, filed Dec. 18, 2019, the contents of which are hereby incorporated by reference in their entirety.

BACKGROUND

Field

The application relates to an instrument for use with a bone anchoring device that includes a receiving part for connecting a bone anchoring element to a rod. The invention further relates to a system including such an instrument and a bone anchoring device. In particular, the instrument may be used to finally tighten or lock a bone anchoring element and/or a rod with respect to the bone anchoring device.

Description of Related Art

US 2006/0293666 A1 describes a counter-holding tool for use with a receiving part of a polyaxial screw. It has a grip portion, a hollow shaft and a holding portion that is configured to be placed over the receiving part. A screwing-in tool can be guided through the hollow shaft.

U.S. Pat. No. 10,349,986 B2 describes a surgical instrument for use with a bone fastener. The instrument includes an outer sleeve that has a drive engageable with a drive socket of the bone fastener. An inner shaft is provided within the outer sleeve and provided with a screw that can be connected to an inner thread of a receiver of the bone fastener. The inner shaft is rotatable relative to the outer sleeve.

SUMMARY

It is an object of the present invention to provide an alternative and/or improved instrument suitable for use with a bone anchoring device and a system including such an instrument and a bone anchoring device, where the instrument is easy to handle, has a reduced size, and/or can be used with different anchoring devices.

An instrument according to an embodiment includes a hollow tube which has at least one protruding portion at an end portion thereof that is configured to engage a recess of the receiving part adapted to accommodate the rod therein. The tube can act as a counter holder for an inner shaft, such as a shaft with a drive portion, for final tightening of a screw. Thus, a rotational movement of the tube relative to the receiving part can be inhibited.

As the at least one protruding portion engages the rod recess of the receiving part, an amount of space or footprint needed by the instrument may be reduced. This permits use of narrow channels through the tissue of the human body to approach the implantation site. Hence, the instrument can be particularly applicable in minimally invasive surgery (MIS).

Moreover, no additional structures or elements are required at an outer surface of the receiving part to prevent the tube from rotating relative to the receiving part. Hence, the structure of the receiving part and/or the tube may be simplified, when compared to the structure of a receiving part and/or tube that engages an outer surface of the receiving part. In particular, the engagement of the tube and the receiving part is implemented by means of the rod recess, which is already provided in the receiving part as an essential feature thereof.

In particular, the tube may be placed within a central passage of the receiving part, with only the at least one protruding portion protruding out of the central passage in a radial direction. Hence, a system including the bone anchoring device and the attached instrument as a whole is slim, which renders the combination useful for MIS.

The tube may in particular have an internal channel that allows the shaft of the instrument, in particular the shaft having an engagement or drive portion, to be advanced through and guided by the tube. This guidance may facilitate engagement of the shaft or an engagement portion provided at its end, such as a drive portion, with an element located within the receiving part, such as a fixation element, for example a set screw.

In a further embodiment, the tube is a first tube, and the instrument includes an additional second tube configured to be arranged outside at least a portion of the receiving part to encompass the respective portion of the receiving part, in particular the legs of the receiving part. Encompassing the receiving part at its outside may provide for additional support and/or guidance of the first tube. The second tube may be very thin. Such a design of reduced thickness renders the instrument more suitable for MIS. If the second tube is arranged substantially around the legs of the receiving part, splaying of the legs may be prevented.

When the second tube is used with a bone anchoring device that has long extensions provided at the legs of the receiving part, the second tube may be configured to substantially encompass merely the legs of the receiving part and not the long extensions. On the other hand, when used with a bone anchoring device without such long extensions, the second tube may serve for prolonging the central passage of the receiving part.

The second tube may be provided as a member separate from the first tube and/or separate from other portions of the instrument. For example, the second tube can be a sleeve used for various surgical steps, such as guiding parts and/or instruments to the implantation site or as a sleeve extension for a receiving part. In this case, the second tube may also have a considerably reduced thickness. At the end of the procedure, the first tube may be inserted into the second tube, and an inner shaft with a drive portion may be used for final tightening of a locking screw.

BRIEF DESCRIPTION OF THE DRAWINGS

Further features and advantages will become apparent from the detailed description of embodiments by means of the accompanying drawings. In the drawings:

FIG. 3a shows an upper perspective view of the rear portion, FIG. 3b shows a lower perspective view of the rear portion, FIG. 3c shows a cross-sectional view of the rear portion, the cross-section taken along line A-A in FIG. 3d, and FIG. 3d shows a plan view of the rear portion from above.

FIG. 4a shows an upper perspective view of the front portion, FIG. 4b shows a lower perspective view of the front portion, FIG. 4c shows a cross-sectional view of the front portion, the cross-section taken along line B-B in FIG. 4d, and FIG. 4d shows a plan view of the front portion from below.

FIG. 5 shows a perspective view of a polyaxial bone anchoring device according to an embodiment in an assembled state, where the polyaxial bone anchoring device is suited for use with the instrument shown in FIGS. 1 to 4d.

FIG. 6 shows an exploded perspective view of the polyaxial bone anchoring device of FIG. 5.

FIGS. 7a to 7c show perspective views of the instrument shown FIGS. 1 to 4d, with the spinal column and polyaxial bone anchoring devices shown in FIGS. 1 and 2, wherein FIGS. 7a to 7c show a use of the instrument.

FIGS. 9a to 9c show cross-sectional views of a portion of the polyaxial bone anchoring device and the instrument shown in FIGS. 7b and 7c.

FIGS. 12a to 12d show different views of a rear portion of an inner tube of the instrument of FIGS. 10 and 11. In particular, FIG. 12a shows an upper perspective view of the rear portion, FIG. 12b shows a lower perspective view of the rear portion, FIG. 12c shows a cross-sectional view of the rear portion, the cross-section taken along line C-C in FIG. 12d, and FIG. 12d shows a plan view of the rear portion from above.

FIGS. 13a to 13c show different views of a front portion of the inner tube of the instrument of FIGS. 10 and 11. In particular, FIG. 13a shows an upper perspective view of the front portion, FIG. 13b shows a lower perspective view of the front portion, and FIG. 13c shows a cross-sectional view of the front portion, the cross-section taken in a plane including a longitudinal axis of the inner tube.

FIG. 14 shows a side view of an outer tube of the instrument of FIGS. 10 and 11.

FIGS. 15a to 15c show different views of an upper portion of the outer tube of FIG. 14 and of a snap ring and a pin of the instrument shown in FIGS. 10 and 11. In particular, FIG. 15a shows an upper perspective view of the upper portion, the snap ring, and the pin, FIG. 15b shows a lower perspective view of the upper portion, the snap ring, and the pin, and FIG. 15c shows a cross-sectional view of the upper portion, the snap ring, and the pin, the cross-section taken in a plane including a longitudinal axis of the outer tube in a state where the snap ring and the pin are coupled to the outer tube.

FIGS. 16a to 16d show different views of a lower portion of the outer tube of FIG. 14. In particular, FIG. 16a shows an upper perspective view of the lower portion, FIG. 16b shows a lower perspective view of the lower portion, FIG. 16c shows a cross-sectional view of the lower portion, the cross-section taken along line D-D in FIG. 16d, and FIG. 16d shows a plan view of the lower portion from below.

FIG. 17 shows a perspective view of a polyaxial bone anchoring device according to a further embodiment in an assembled state, where the polyaxial bone anchoring device is suited for use with the instrument shown in FIGS. 10 to 16d.

FIG. 18 shows an exploded perspective view of the polyaxial bone anchoring device of FIG. 17.

DETAILED DESCRIPTION

Figure 1:
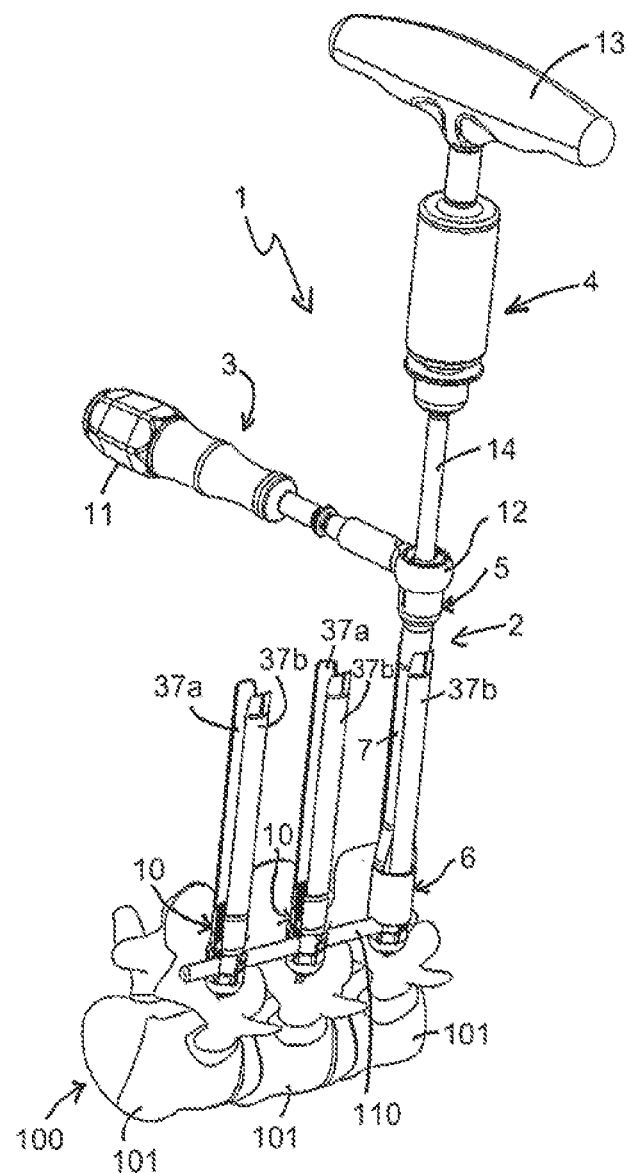
FIG. 1 shows a perspective view of a part of a spinal column with a plurality of polyaxial bone anchoring devices and an instrument according to a first embodiment of the present disclosure coupled to one of the polyaxial bone anchoring devices.
Figure 2:
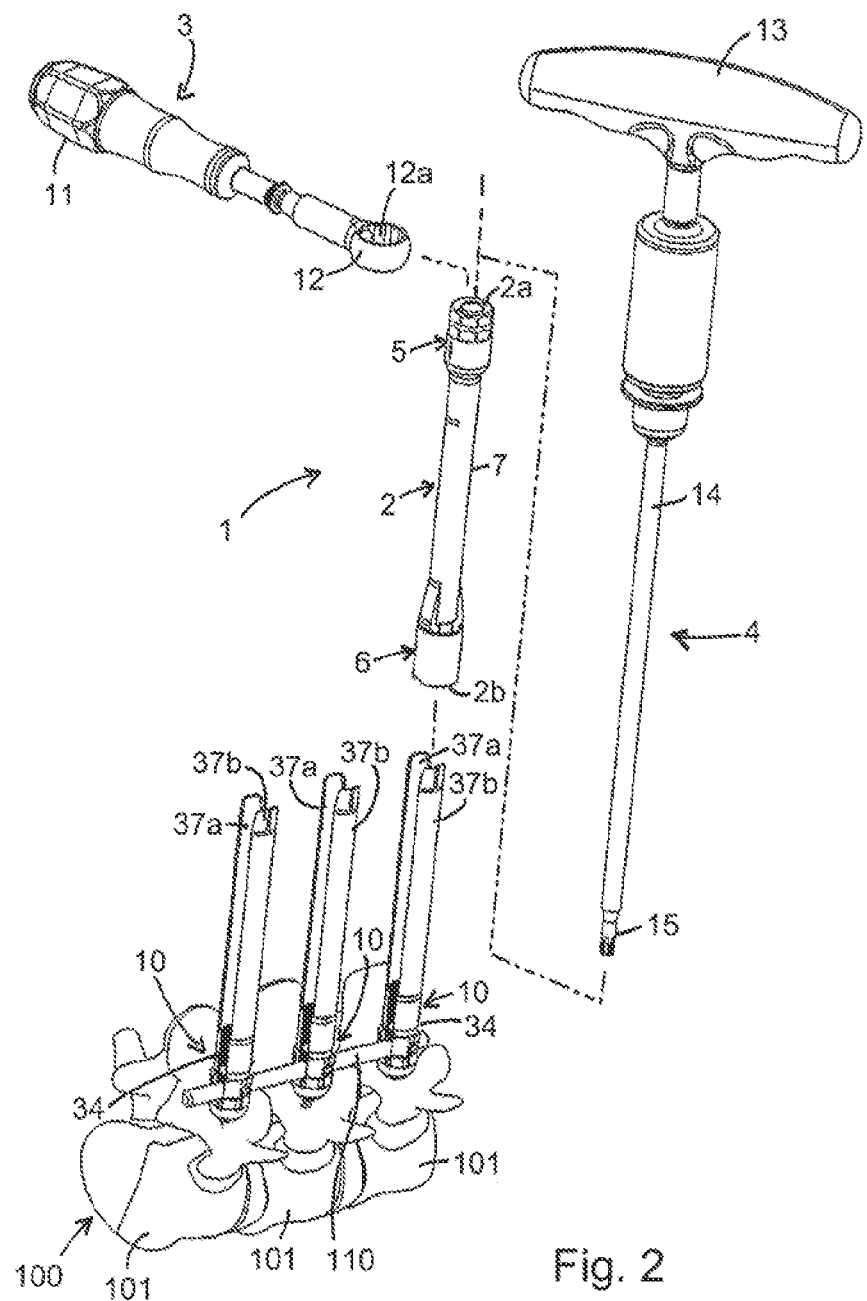
FIG. 2 shows an exploded perspective view of the instrument of FIG. 1.

Referring to FIGS. 1 and 2, the instrument 1 of a first embodiment includes a tube member 2, a grip member 3, and a screwing-in tool such as a screw driver 4. FIGS. 1 and 2 further show a plurality of vertebral bodies 101 of a spinal column 100, each vertebral body 101 being provided with a bone anchoring device 10 inserted into the respective vertebral body 101. The bone anchoring devices 10 are connected to one another by means of a rod 110. The bone anchoring device 10 will be described further below with reference to FIGS. 5 and 6.

Returning to the instrument 1, the tube member 2 extends between a rear end 2a and a front end 2b along a longitudinal axis I. Adjacent to the rear end 2a, the tube member 2 has a rear portion 5, which is configured to be coupled to the grip member 3. Furthermore, the tube member 2 has a front portion 6 adjacent the front end 2b, where the front portion 6 is configured to be coupled to a receiving part 34 of the bone anchoring device 10. Coupling of the tube member 2 to the bone anchoring device 10 will be explained in greater detail below. A middle portion 7 of the tube member 2 is disposed between the rear portion 5 and the front portion 6 along the longitudinal axis I.

The grip member 3 includes a grip portion formed as a handle 11 and an engagement portion 12 for engagement with the rear portion 5 of the tube member 2. The engagement portion 12 depicted in FIGS. 1 and 2 has a through-hole 12a for form fit engagement with the rear portion 5, and can be, for example, shaped as a polygon such as an octagon. In the engaged state, as shown in FIG. 1, the handle 11 may be arranged substantially perpendicular to the longitudinal axis I of the tube member 2.

The screw driver 4 includes a grip portion formed as a handle 13 and a shaft 14 extending therefrom. At an end of the shaft 14 opposite to the handle 13, a drive portion 15 is provided that is configured to engage a screw member provided within the receiving part 34 of the bone anchoring device 10, and in particular, a fixation element described further below. The shaft 14 of the screw driver 4 is configured to be received in the tube member 2, such that at least the handle 13 of the screw driver 4 protrudes from the tube member 2 and the shaft 14 is displaceable within the tube member 2 along its longitudinal axis I.

Hereafter, the tube member 2 is described in greater detail with reference to FIGS. 3a to 4d. FIGS. 3a to 3d show views of the rear portion 5 and a part of the middle portion 7, whereas FIGS. 4a to 4d show views of the front portion 6 and a part of the middle portion 7.

The tube member 2 includes a first tube 16 that extends between the rear end 2a and the front end 2b along the longitudinal axis I of the tube member 2. The first tube 16 has an inner surface 16a that forms an internal channel 17 of the tube member 2. The internal channel 17 has a cylinder shape, with its axis extending along the longitudinal axis I of the tube member 2 and a diameter d1 that is substantially constant along the longitudinal axis I. The internal channel 17 is open to the rear end 2a as well as to the front end 2b of the tube member 2, and thus forms an open central passage through the tube member 2. The internal channel 17 is shaped so as to accommodate at least a portion of the shaft 14 of the screw driver 4 therein and to guide the shaft 14 therethrough. In particular, the diameter dl of the internal channel substantially corresponds to an outer diameter of the shaft 14 of the screw driver 4 or is slightly greater than the outer diameter of the shaft 14.

The middle portion 7 of the tube member 2 is formed by a part of the first tube 16 that has a cylindrical outer shape, and preferably has a substantially constant cross section along the longitudinal axis I, in particular a constant outer diameter d2. The outer diameter d2 is selected such that the middle portion 7 is configured to be received in a space formed between two extensions 37a, 37b of the polyaxial bone anchoring device, shown in FIGS. 1-2 and 5-6, and serve to provide an extension for a coaxial bore of the receiving part 34. In particular, the outer diameter d2 of the first tube 16 at the middle portion 7 may be slightly less than a distance between the two extensions 37a, 37b, i.e., a diameter or width of the coaxial bore of the receiving part 34, such that the tube member 2 can be guided by the extensions 37a, 37b.

Referring to FIGS. 3a to 3d, the rear portion 5 of the tube member 2 includes a widened section of the first tube 16. The rear portion 5 has a cylindrical section 18 and an engagement section 19. The engagement section 19 has an outer shape in a circumferential direction which corresponds to the inner shape of the through-hole 12a of the grip member 3, to provide a form-fit engagement. Preferably a polygonal, such as an octagonal, shape is used. Thus, the engagement section 19 is configured to enter the through-hole 12a of the grip member 3 to connect the grip member 3 and the tube member 2. The form-fit engagement prevents rotation of the grip member 3 relative to the tube member 2 around the longitudinal axis I. Preferably a length of the engagement section 19 in the direction of the longitudinal axis I substantially corresponds to a length of the through-hole 12a of the grip member 3 in an axial direction of the through-hole 12a. Thus, the entire engagement section 19 may be received within the through-hole 12a of the grip member 3. A circumferential groove 19c may divide the engagement section 19 into an upper engagement section 19a and a lower engagement section 19b along the longitudinal axis I. The upper engagement section 19a is located adjacent the rear end 2a of the tube member 2 and the lower engagement section 19b is located adjacent the cylindrical section 18. The circumferential groove 19c may, for example, engage a protrusion (not shown in the figures) formed in the inner surface of the through-hole 12a of the grip member 3, to better retain the grip member at a set axial position relative to the tube member 2.

Figure 3A:
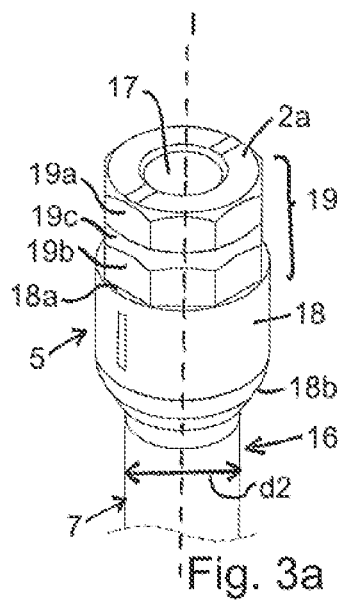
FIGS. 3a to 3d show different views of a rear portion of a tube member of the instrument of FIGS. 1 and 2. In particular.
Figure 3B:
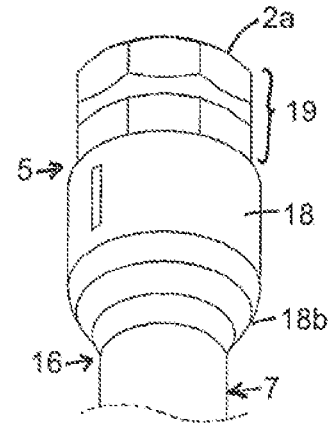
Figure 3C:
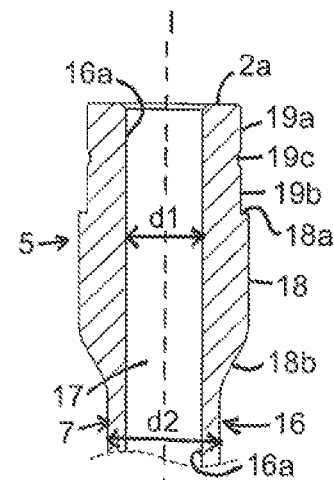
Figure 3D:
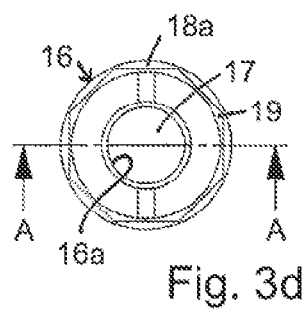

The cylindrical section 18 has an outer diameter that is greater than an outer diameter of at least part of the engagement section 19, so as to form a shoulder 18a at a transition between the engagement section 19 and the cylindrical section 18. The shoulder 18a forms a stop for the engagement portion 12 of the grip member 3, in order to prevent the grip member 3 from advancing beyond the shoulder 18a in a direction towards the front end 2b of the tube member 2. The cylindrical section 18 has an outer diameter that may exceed the outer diameter d2 of the first tube 16 at the middle portion 7. A transition 18b between the cylindrical section 18 and the middle portion 7 may be a smooth transition as shown in FIGS. 3a to 3c.

Figure 4D:
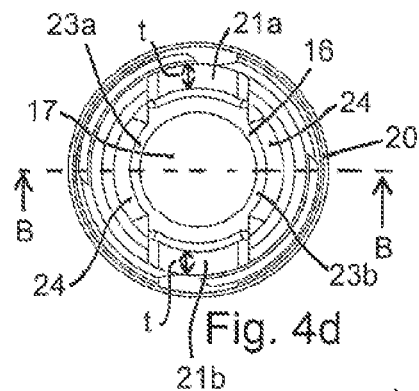
FIGS. 4a to 4d show different views of a front portion of the tube member of the instrument of FIGS. 1 and 2. In particular.
Figure 4A:
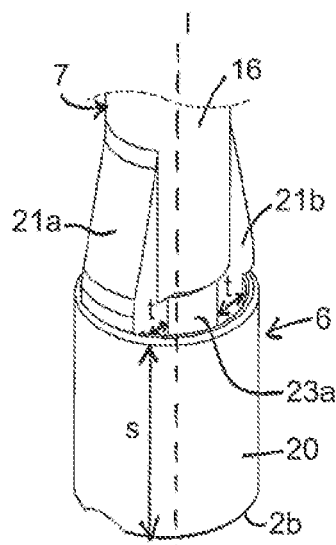
Figure 4B:
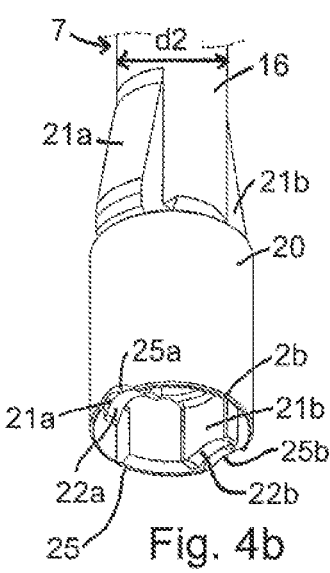
Figure 4C:
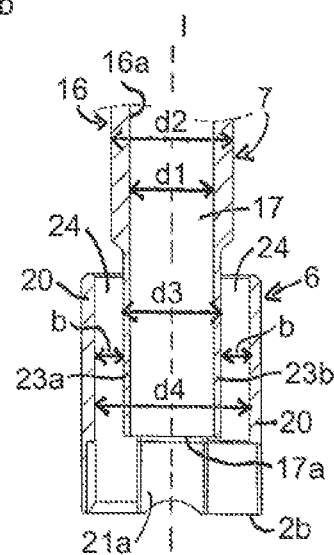

Referring now to FIGS. 4a to 4d, the front portion 6 of the tube member 2 is formed by the first tube 16 and a second tube 20 provided around the first tube 16. As best seen in FIG. 4c, the first tube 16 has a reduced outer diameter d3 at the front portion 6 that is less than the outer diameter d2 of the first tube 16 at the middle portion 7. The internal channel 17 ends at an end 17a at a distance from the front end 2b of the tube member 2, i.e., the internal channel does not extend all the way to the front end 2b. The first tube 16 includes a first protruding portion 21a and a second protruding portion 21b that each project radially outward from an outer surface of the first tube 16 at least at the front portion 6 of the tube member 2. The protruding portions 21a, 21b also project axially from the end 17a parallel to the longitudinal axis I up to the front end 2b of the tube member 2. The first and second protruding portions are each located in a circumferential direction of the tube member 2 and shaped such that they are configured to enter a recess for the rod 110 formed in the receiving part 34 of the polyaxial bone anchoring device 10 (see FIGS. 5 and 6). In particular, the first protruding portion 21a and the second protruding portion 21b are arranged on opposite sides along the circumferential direction of the first tube 16, and each have a width along the circumferential direction of the first tube 16 that substantially corresponds to a width of the recess of the receiving part 34. In particular, a thickness t of the first and second protruding portions 21a, 21b in a radial direction of the first tube 16 perpendicular to the longitudinal axis I, may be at least a thickness or substantially equal to the thickness of the wall (or the legs) of the receiving part 34 perpendicular to the central axis. A length of the first and second protruding portions 21a, 21b along the longitudinal axis I substantially corresponds to a height of the recess of the receiving part 34 between an upper or first end of the receiving part and an inserted rod 110.

The first and second protruding portions 21a, 21b each has a cylindrical recess that forms respective first and second front surfaces 22a, 22b at the front end 2b of the tube member 2. A radius of said cylindrical recess substantially corresponds to a radius of the rod 110 of the polyaxial bone anchoring device 10.

Furthermore, at the front portion 6, the first tube 16 forms first and second intermediate portions 23a, 23b that are located at circumferential positions of the first tube 16 where the protruding portions 21a, 21b are not provided. Hence, the intermediate portions 23a, 23b are each located between the first and second protruding portions 21a, 21b in a circumferential direction of the first tube 16. When the first and second protruding portions 21a, 21b enter the recess formed in the receiving part 34, as explained above, the intermediate portions 23a, 23b may thus be located at those circumferential positions that correspond to the positions of the legs of the receiving part formed by the recess.

The second tube 20 extends along the longitudinal axis I from the front end 2b of the tube member 2 to a distance thereof. In particular, the second tube 20 extends for a length s along the longitudinal axis I. The second tube 20 is firmly attached to the projecting portions 21a, 21b of the first tube 16, or is monolithically provided with the first tube 16, wherein the projecting portions 21a, 21b form connecting portions that connect the first tube 16 and the second tube 20. A shape of the second tube 20 may be cylindrical. The second tube 20 is configured to be arranged around the receiving part 34. In particular, an inner diameter d4 of the second tube 20 is greater than an outer diameter of the receiving part 34. The inner diameter d4 of the second tube 20 is also greater than the outer diameter d3 of the first tube 16, so that a gap 24 is provided between outer surfaces of the intermediate portions 23a, 23b of the first tube 16 and the inner surface of the second tube 20. The width b of the gap 24 in the radial direction perpendicular to the longitudinal axis I is selected such that the legs of the receiving part 34, as well as the extensions 37a, 37b, can be received within the gap 24. In particular, the width b of the gap 24 substantially corresponds to a thickness of the wall (or legs) of the receiving part 34 measured perpendicular to the central axis.

Furthermore, the second tube 20 has a front surface 25 at the front end 2a of the tube member 2. Cylindrical recesses 25a, 25b are provided at the front surface 25 at positions that correspond to the positions of the projecting portions 21a, 21b in the circumferential direction. A radius of said cylindrical recesses substantially corresponds to a radius of the rod 110 of the polyaxial bone anchoring device 10.

Next, with reference to FIGS. 5 and 6, an example of a polyaxial bone anchoring device that is suitable for use with the instrument 1 will be explained. The polyaxial bone anchoring device 10 according to an embodiment includes a bone anchoring element 30 with a shank 31 and a head 32 having a spherically-shaped outer surface portion. The bone anchoring element 30 may be a bone screw with a threaded shank. The head 32 may have a recess 33 that is provided for engagement with a tool, such as a driver. A receiving part 34 is adapted for receiving the head 32 and for connecting the bone anchoring element 30 to the rod 110. In addition, a fixation element 35 in the form of an inner screw or a set screw is provided for fixing the rod 110 in the receiving part 34. The fixation element 35 has a recess 35a for engagement with the drive portion 15 of the screw driver 4 and an outer thread 35b. Also, the bone anchoring device 10 includes a locking ring 36 for locking the head 32 in the receiving part 34. The bone anchoring device 10 further includes first and second extensions 37a, 37b connected to the receiving part 34.

The receiving part 34 has a first or upper end 34a and a second or lower end 34b. Adjacent to the upper end 34a, a rod receiving portion 38 is provided, and adjacent to the lower end 34b, a head receiving portion 39 is provided. The rod receiving portion 38 is substantially cylindrical and has a central passage formed as a coaxial bore 40 that extends from the upper end 34a into the head receiving portion 39 along a central axis C. The bore 40 has an internal thread 40a in at least a portion thereof that cooperates with the outer thread 35b of the fixation element 35. A substantially U-shaped recess 41 that forms a channel for receiving the rod 110 extends from the upper end 34a to almost the beginning of the head receiving portion 39. The recess 41 defines a first leg 45a and a second leg 45b of the receiving part. At a distance from the upper end 34a, a groove or otherwise weakened section 42 may be formed that allows breaking off of the upper portions of the receiving part formed by the U-shaped recess that serve as extended tabs. The first and second extensions 37a, 37b are provided at the first and second legs 45a, 45b, respectively, and extend beyond the upper edge 34a of the receiving part parallel the central axis C. The extensions 37a, 37b extend or form a continuation of the bore 40 beyond the receiving part 34, and may be useful for minimally invasive surgeries (MIS).

The head receiving portion 39 has a substantially cap-like shape with a hollow substantially spherical interior portion (not shown in the figures) for receiving the head 32 pivotably therein. A plurality of slits 46 render the head receiving portion flexible, so that when pressure is exerted onto the head receiving portion 39 by the locking ring 36, the head 32 can be clamped and finally locked.

The locking ring 36 is designed to encompass the head receiving portion 39 and has an internal surface structure that cooperates with the head receiving portion 39 to provide a full locking of the head 32 in the head receiving portion 39 when the locking ring 36 is at a lowermost position, and a pre-locking when the locking ring 36 is at a position slightly above the lowermost position, where pivoting of the head 32 in the head receiving portion is still possible but removal of the head 32 from the head receiving portion 39 is prevented. The locking ring 36 further has upstanding slightly flexible sections 47 that may serve for engagement with the receiving part to preliminarily hold the locking ring in a pre-locking position. Also, two opposing ones of said projections 47 may be provided at an upper side of the locking ring for supporting the rod 110. In the embodiment shown, the locking ring 36 also includes two upstanding arms 48 that are arranged on opposite sides of the locking ring. The upstanding arms may provide for engagement of the locking ring with a further instrument (not shown in the figures) other than the instrument 1 described above.

Use of the instrument 1 will now be explained, with reference to FIGS. 7a to 9c. The bone anchoring element 30 may be implanted in a vertebra 101 or other bone. The locking ring 36 may be at an axial position where the head 32 is locked in the head receiving portion 39. In this position, the rod 110 located in the substantially U-shaped recess 41 is still movable. Also, the fixation element 35 may already be screwed into the bore 40 of the receiving part 34 but not yet tightened.

Figure 7C:
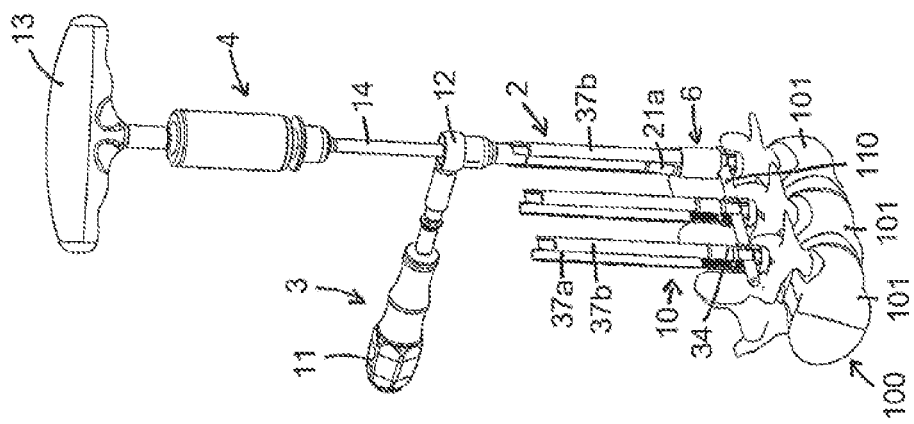
Figure 7B:
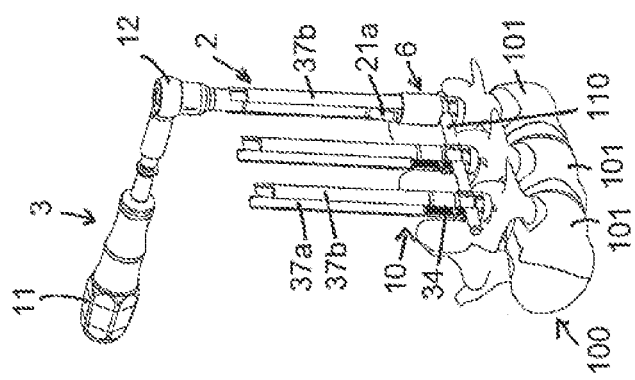
Figure 7A:
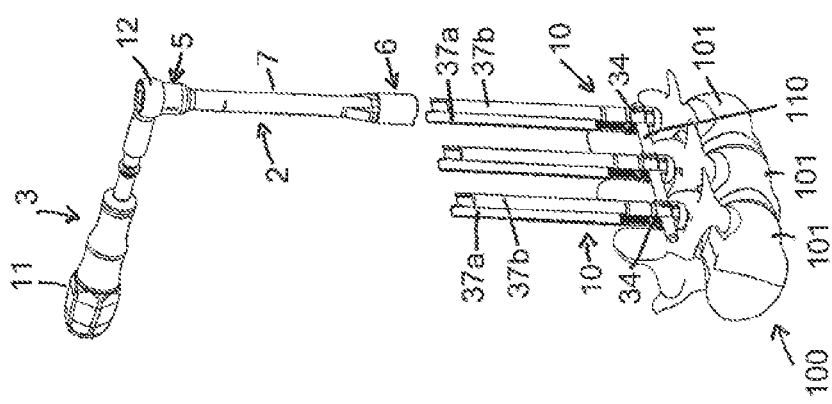
Figure 8A:
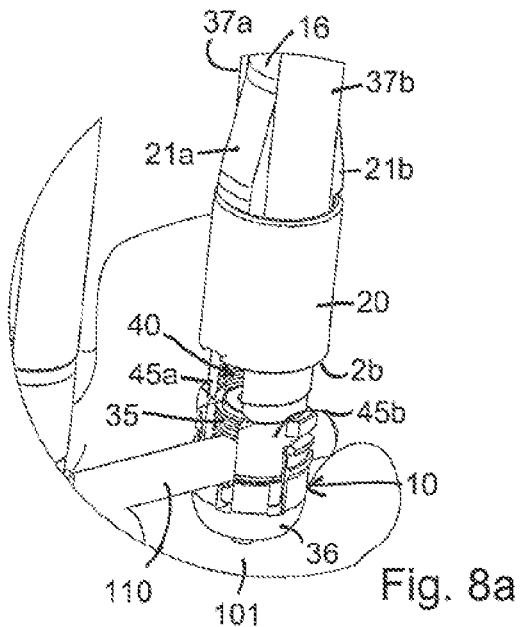
FIGS. 8a and 8b are enlarged views of a portion of the polyaxial bone anchoring device and the instrument shown in FIGS. 7b and 7c, to show steps of coupling the instrument to the polyaxial bone anchoring device in greater detail.

Referring to FIGS. 7a, 8a, and 9a, the tube member 2 with the grip member 3 is attached to a polyaxial bone anchoring device 10. To do so, the front end 2b of the tube member 2 is advanced over the free ends of the extensions 37a, 37b, so that the first tube 16 is located at a position of the bore 40, i.e., in the space formed between the extensions 37a and 37b, and the second tube 20 is located around the extensions 37a, 37b. The protruding portions 21a, 21b protrude out of the space formed between the extensions 37a, 37b at circumferential positions that correspond to the recess 41 of the receiving part 34. Next, the tube member 2 is advanced along the central axis C towards the bone anchoring element 30 until its front end 2b contacts the inserted rod 110. In doing so, the first tube 16 advances within the space formed between the extensions 37a, 37b and is guided by the extensions 37a, 37b. Further guidance of the tube member 2 is provided by the second tube 20 sliding along the outer surfaces of the extensions 37a, 37b. The tube member 2 may be held and advanced manually by an operator such as a surgeon who holds the handle 11.

Figure 8B:
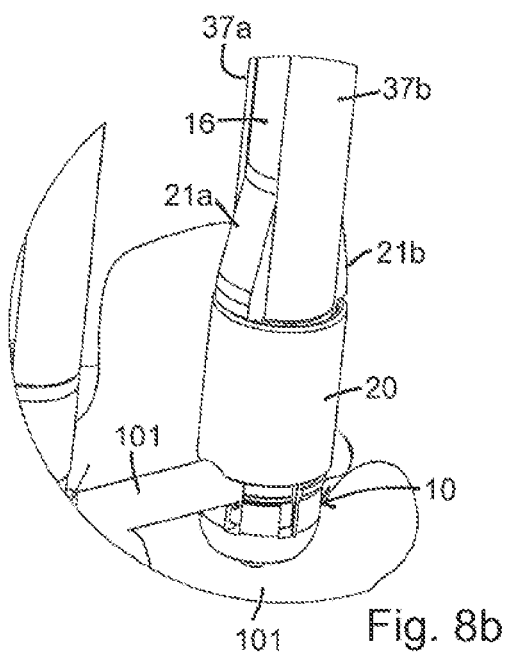

The final position of the tube member 2, in which the front end 2b contacts the inserted rod 110, is shown in FIGS. 7b, 8b and 9b. In this position, the protruding portions 21a, 21b of the first tube 16 are arranged within the substantially U-shaped recess 41 of the receiving part 34, and preferably abut against the lateral sides of the recess 41. Hence, the tube member 2 is prevented from rotating relative to the receiving part 34 around the longitudinal axis I. The front surfaces 22a, 22b of the protruding portions 21a, 21b and the front surface 25 of the second tube 20 abut against the inserted rod 110. The legs 45a, 45b of the receiving part 34 are provided within the gap 24 of the tube member 2 formed between the first tube 16 and the second tub 20 at the positions of the intermediate portions 23a, 23b. The internal channel 17 extends through the tube member 2 from its rear end 2a to the end 17a of the channel located at or slightly above the fixation element 35.

Next, as shown in FIGS. 7c and 9c, the shaft 14 of the screw driver 4 is introduced into the internal channel 17 of the tube member 2 at its rear end 2a and advanced through and guided by the channel 17 towards the front end 2b, until the drive portion 15 of the screw driver 4 exits the channel 17 at its end 17a and engages the recess 35a of the fixation element 35. The fixation element 35 can then be tightened by rotating the handle 13, and thus also the drive portion 15 of the screw driver 4, around the longitudinal axis I. While rotating the handle 13 of the screw driver 4, in particular manually rotating the handle 13, the tube portion 2 may be held, e.g. manually held, at its handle 11 to act as a counter holder while tightening the fixation element 35. By tightening the fixation element 35, the rod 110 is locked within the receiving part 34, thus locking the relative position of the rod 110 and the bone anchoring element 30.

Figure 10:
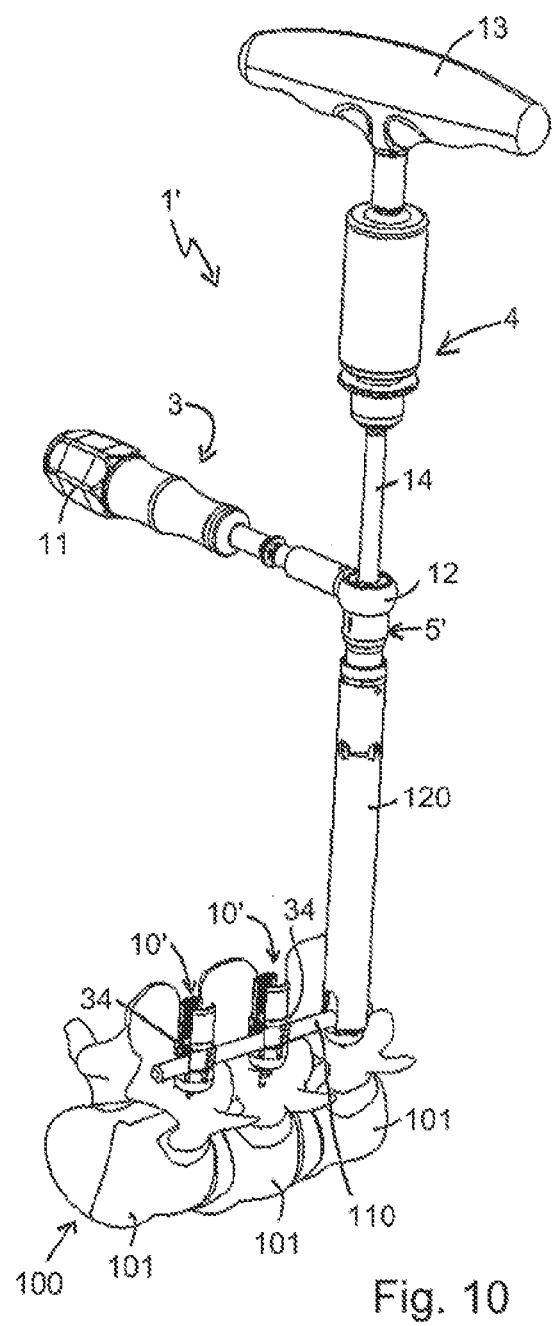
FIG. 10 shows a perspective view of a part of a spinal column with a plurality of polyaxial bone anchoring devices and an instrument according to a second embodiment of the present disclosure coupled to one of the polyaxial bone anchoring devices.
Figure 11:
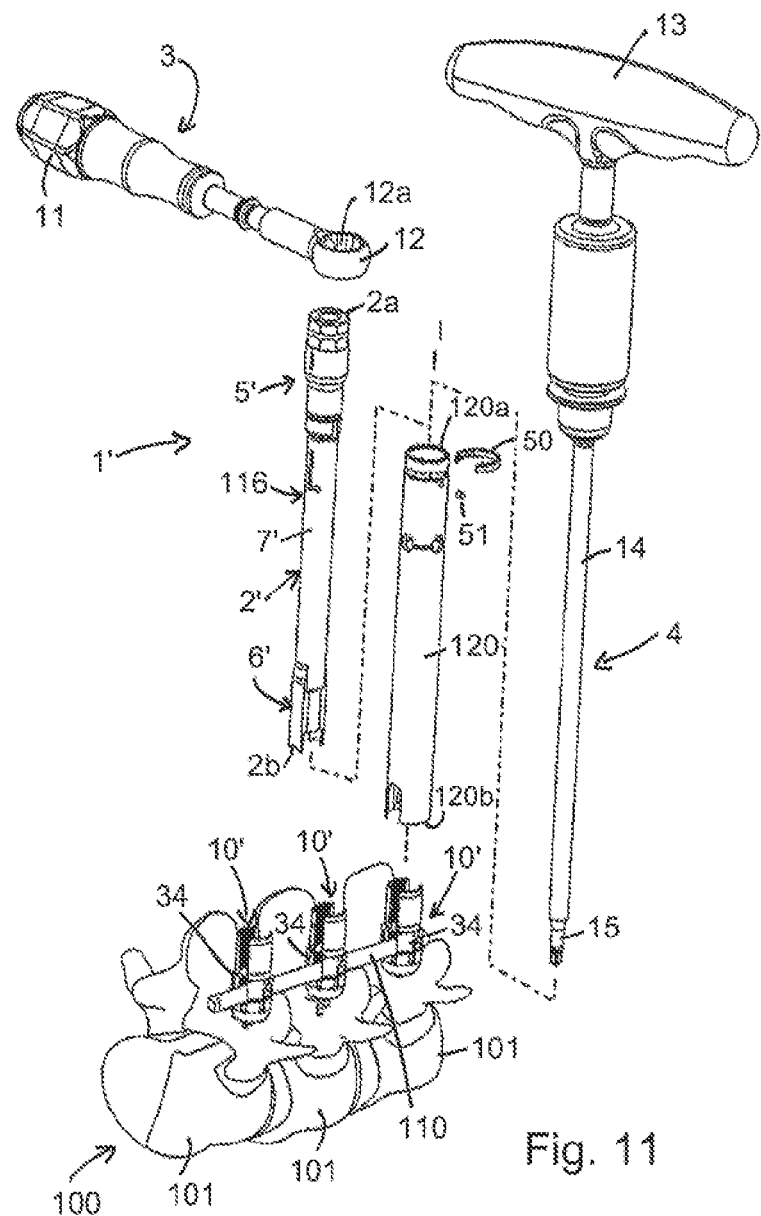
FIG. 11 shows an exploded perspective view of the instrument of FIG. 10.
Figure 19A:
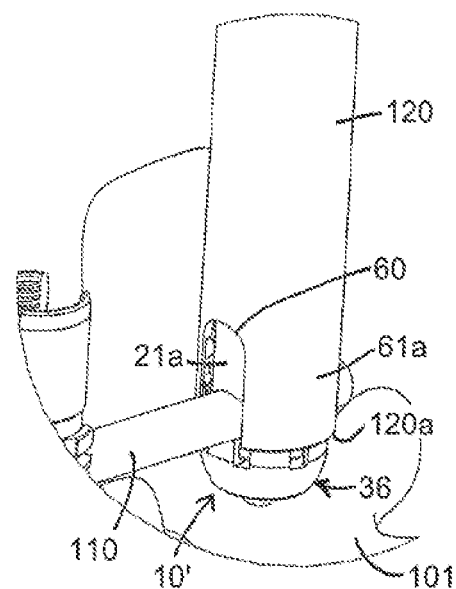
FIGS. 19a and 19b are enlarged perspective views of a lower portion of the instrument shown in FIGS. 10 to 16d and a portion of the polyaxial bone anchoring device inserted into a part of a spinal column to show a use of the instrument, wherein in FIG. 19b, the outer tube is shown in an upper position to provide a better view of the inner tube.
Figure 19B:
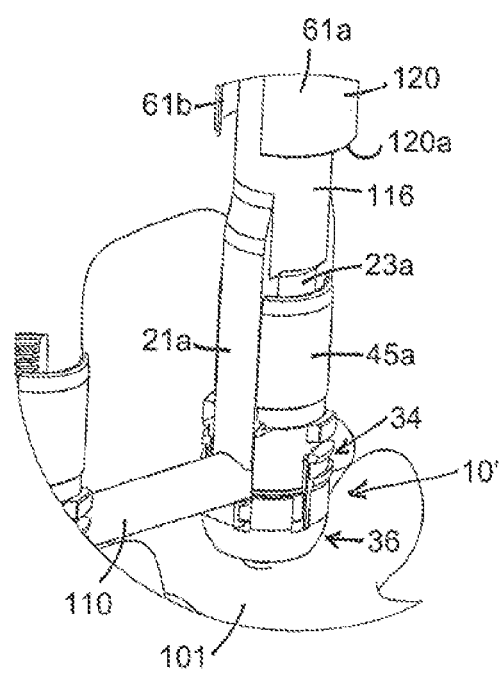

A second embodiment of the instrument is shown in FIGS. 10 to 16d. For the sake of brevity, the description of parts and portions of the instrument of the second embodiment that are the same as or similar to parts and portions of the instrument of the first embodiment described above will not be repeated. The tube member 2' of the instrument 1' of the second embodiment differs from that of the instrument of the first embodiment. Referring to FIGS. 10 and 11, the tube member 2' according to the second embodiment includes a first or inner tube 116 and a second or outer tube 120, as well as a snap ring 50 and a pin 51. It shall be noted that the outer tube 120 may be a part that is used for other surgical procedures and may be combined with the inner tube to form an instrument according to the second embodiment. Such an outer tube may be used, for example, for guiding other parts or instruments to the implantation site or as extension for a receiving part. The outer tube 120 extends from an upper or first end 120a to a lower or second end 120b, and forms a hollow shaft configured to receive the inner tube 116 therein. A length of the second tube 120 measured between its first end 120a and its second end 120b is less than a length of the inner tube 116 measured between its rear end 2a and its front end 2b. In particular, the length of the second tube 120 is selected such that at least the cylindrical section 18 and the engagement section 19 of the rear portion 5' of the inner tube 116 protrude from the first end 120a of the outer tube 120 in an assembled state, i.e., when the inner tube 116 is located within the outer tube 120.

With reference to FIGS. 12a to 13c, the inner tube 116 will now be described. Referring first to FIGS. 12a to 12d, The rear portion 5' of the inner tube 116 differs from the rear portion of the tube member of the first embodiment described above in that the inner tube 116 includes a further cylindrical section 118 arranged below the transition 18b, i.e., adjacent to the transition 18b closer to the front end 2b along the longitudinal axis I. An outer surface of the cylindrical section 118 has a substantially constant outer diameter that is greater than the outer diameter d2 of the middle portion 7' of the inner tube 116. The outer diameter of the cylindrical section 118 substantially corresponds to an inner diameter d5 of the outer tube 120 (see below), or is slightly smaller than the inner diameter d5 of the outer tube 120, so that the outer surface of the cylindrical section 118 is configured to contact an inner surface of the outer tube 120. A circumferential groove 118c divides the cylindrical section 118 into an upper cylindrical section 118a and a lower cylindrical section 118b along the longitudinal axis I. Preferably, the circumferential groove 118c extends along the entire circumference of the cylindrical section 118. The upper cylindrical section 118a is located adjacent the transition 18b and the lower cylindrical section 118b is located adjacent the middle portion 7' of the inner tube 116. Furthermore, a longitudinal recess 118d is formed in the outer surface of the lower cylindrical section 118b. The longitudinal recess 118d may extend along the entire length of the lower cylindrical section 118b along the longitudinal axis I, i.e., from the circumferential groove 118c to the middle portion 7' of the inner tube 116. The longitudinal recess 118d preferably does not extend through the entire thickness of the inner tube 116 in its radial direction, i.e., does not form a transversely open slit of the inner tube. The longitudinal recess 118d is configured to receive the pin 51 therein when the pin 51 extends through and protrudes out of a hole of the outer tube 120.

Referring now to FIGS. 13a to 13c, the front portion 6' of the tube member 2' differs from the front portion of the first embodiment in that it is formed by the inner tube 116 alone. Hence, the protrusion portions 21a, 21b and the intermediate portions 23a, 23b are not enclosed by a tubular portion.

Next, the outer tube 120 will be described with reference to FIGS. 14 to 16d. The outer tube 120 has a substantially cylindrical outer shape and has an inner surface 117a that forms an internal channel 117 of the outer tube 120. The internal channel 117 extends from the first end 120a to the second end 120b in a longitudinal direction of the outer tube corresponding to the direction of the longitudinal axis I of the instrument 1' in an assembled state. The internal channel 117 has a substantially cylindrical shape with an inner diameter d5 that is substantially constant along the entire length of the outer tube 120 in the longitudinal direction. The inner diameter d5 of the internal channel 117 of the outer tube 120 substantially corresponds to the outer diameter d2 of the inner tube 116 at the middle portion 7' of the inner tube 116 or is slightly greater than the outer diameter d2 of the inner tube 116, to permit the inner tube 116 to be guided within the internal channel 117 of the outer tube 120. Furthermore, the inner diameter d5 of the internal channel 117 substantially corresponds to an outer diameter of the receiving part 34 of the polyaxial bone anchoring device 10' or is slightly greater than the outer diameter of the receiving part 34, to accommodate at least a portion of the receiving part 34, in particular its legs, within the internal channel 117.

As shown in FIGS. 15a to 15c, the outer tube 120 has an upper portion adjacent its first end 120a. A groove 52 is provided in the upper portion of the outer tube 120. The groove 52 is configured to receive the snap ring 50 therein. With respect to the direction of the longitudinal axis I, the groove 52 is provided at an axial position that corresponds to the axial position of the groove 118c provided in the cylindrical section 118 of the inner tube 116 described above. The snap ring 50 is an open ring having ends 54a, 54b in a circumferential direction of the ring. Moreover, the snap ring 50 is provided with first and second protrusions 50a, 50b formed at a distance from the respective ends 54a, 54b at an inner surface of the ring. The first and second protrusions 50a, 50b protrude further into an interior region enclosed by the ring than non-protruding portions of the ring adjacent the protrusions. In the present embodiment, the first and second protrusions 50a, 50b are arranged opposed to one another. Due to the shape of the snap ring 50 as an open ring, the snap ring 50 is resilient.

Referring back to the outer tube 120, the groove 52 extends along a circumferential portion of the outer tube 120 but does not encompass the entire circumference of the outer tube 120. The groove 52 may extend around approximately three quarters, i.e., around 270°, of the circumference of the outer tube 120, for example. The circumferential length of the groove 52 corresponds to a circumferential length of the snap ring 50 between the ends 54a, 54b. Furthermore, a first opening 52a and a second opening 52b are formed in the groove 52 to receive the protrusions 50a, 50b of the snap ring 50 therein. The openings 52a, 52b are through-holes that extend from an outer surface of the outer tube 120 through its wall to the internal channel 117, whereas portions of the groove 52 aside from the openings 52a, 52b do not extend entirely through the wall of the outer tube 120 in the radial direction. At a distance below the groove 52, i.e., further towards the second end 120b in the direction of the longitudinal axis I, a through-hole 53 is provided that extends from an outer surface of the outer tube 120 through its wall to the internal channel 117. The through-hole 53 is shaped to receive the pin 51 therein. The through-hole 53 is located at a position of the outer tube 120 such that the pin 53 inserted into the through-hole 53 extends into the longitudinal recess 118d of the lower cylindrical section 118b of the inner tube 116 described above.

Figure 20A:
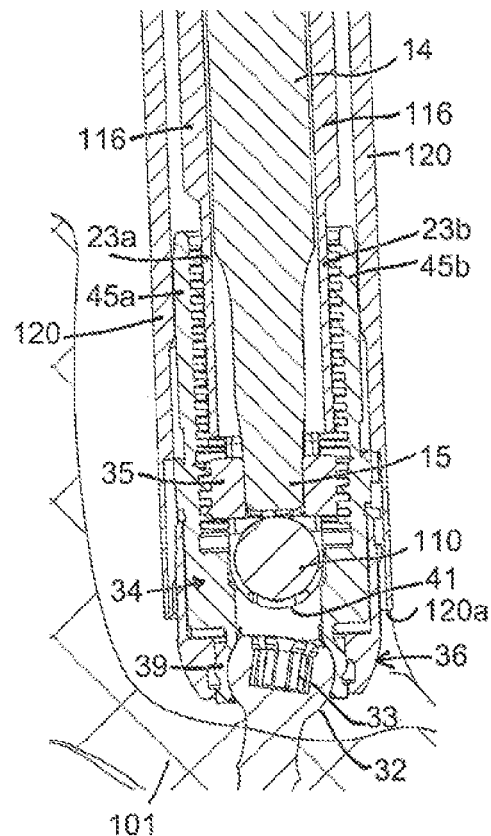
FIGS. 20a and 20b show cross-sectional views of the lower and upper portions, respectively, of the polyaxial bone anchoring device and the instrument shown in FIGS. 10, 11, 19a, and 19b to show a use of the instrument.
Figure 20B:
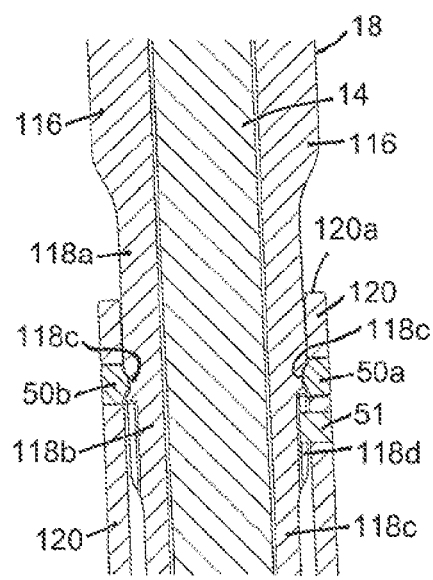

As shown in FIG. 15c, when the snap ring 50 is arranged in the groove 50, the protrusions 50a, 50b of the snap ring 50 extent through the respective openings 52a, 52b of the groove 52 into the internal channel 117 of the outer tube 120. Likewise, the pin 51 extends through the through-hole 53 into the internal channel 117. Hence, in the assembled state of the instrument 1' as shown in FIGS. 10 and 20b, the inner tube 116 is located within the channel 117 of the outer tube 120, while the grip member 3 is attached to the engagement section 19 of the inner tube 116 which protrudes away from the first end 120a of the outer tube 120. The first and second protrusions 50a, 50b of the snap ring 50 provided within the groove 52 of the outer tube 120 extend through the openings 52a, 52b of the groove 52, respectively, and engage the circumferential groove 118c provided in the outer surface of the inner tube 116. The pin 51 extends through the through-hole 53 of the outer tube 120 and engages the longitudinal recess 118d provided in the outer surface of the inner tube 116. As the protrusions 50a, 50b of the snap ring 50 and the pin 53 protrude inwardly from the outer tube 120 and extend into indentations (i.e., the groove 118c and the recess 118d) provided in the outer surface of the inner tube 116, translational and rotational movement of the inner tube 116 relative to the outer tube 120 is inhibited. Thus, the position of the inner tube 116 relative to the outer tube 120 can be locked.

Turning now to FIGS. 16a to 16d, the outer tube 120 further has a recess 60 adjacent its second end 120b to accommodate the rod 110 therein. The recess forms first and second legs 61a, 61b of the outer tube adjacent its second end 120b. A distance between the first leg 61a and the second leg 61b, i.e., a width of the recess 60 in the circumferential direction of the outer tube 120, substantially corresponds to a diameter of the rod 110 or is slightly greater than the diameter of the rod. In the direction of the longitudinal axis I, a depth of the recess 60 is preferably greater than the diameter of the rod 110. When the outer tube 120 is arranged around the legs of the receiving part 34 of the polyaxial bone anchoring device 10' as shown in FIG. 10, the rod 110 is located in the recess 60 of the outer tube 120.

The instrument 1' of the second embodiment is suited for use with a polyaxial bone anchoring device 10' depicted in greater detail in FIGS. 17 and 18. This polyaxial bone anchoring device 10' differs from the polyaxial bone anchoring device 10 for use with the instrument of the first embodiment described above in that the extensions 37a, 37b (see FIGS. 5, 6) are omitted. Hence, the outer tube 120 of the instrument 1' of the second embodiment can serve as an extension of the coaxial bore 40 of the receiving part 34.

Use of the instrument 1' of the second embodiment can be substantially similar to the use of the instrument 1 of the first embodiment, and is shown in FIGS. 19a to 20b. Instead of providing the second tube 20 of the tube member 2 of the first embodiment to encompass the legs 45a, 45b of the receiving part 34, in the second embodiment, the outer tube 120 is provided to encompass the legs 45a, 45b, and serve to extend the coaxial bore 40 beyond the receiving part 34 in the direction of the longitudinal axis I, to provide for additional stabilization and guidance of the inner tube 116. When assembling the instrument 1', first the outer tube 120 is placed on and around the receiving part 34 and subsequently the inner tube 116 is inserted into the channel 117 of the outer tube and coupled to the outer tube by means of the snap ring 50 and the pin 51.

It should be noted that, instead of providing the snap ring 50 and pin 51 used for coupling the outer tube 120 to the inner tube 116, any other suitable means or elements, such as a screw or any other detachable or non-detachable connection, may be used for coupling the tubes to one another. Alternatively, the first tube 116 may be integrally provided with the second tube 120.

In the second embodiment described above, the outer tube 120 forms part of the instrument 1'. However, in a modification of the second embodiment, the instrument 1' may only include the inner tube 116, the grip member 3, and the screw driver 4. In this case, the outer tube 120, the snap ring 50, and the pin 51 may be provided as parts separate from the instrument. In particular, in this case, the outer tube 120 may also be used for other purposes, or with any other tools or instruments, in order to provide a channel that extends from the first end 120a to the receiving part 34, i.e., that serves to extend the coaxial bore 40 of the receiving part 34 to thus, for example, provide guidance for tools or instruments, etc. It should be noted that the instrument of the second embodiment may also be used without the outer tube 120. Likewise, the tube member 2 of the instrument 1 of the first embodiment may also be provided without the second tube 20.

Further modifications of the embodiments described above are also possible without deviating from the scope of the present disclosure. For example, the instrument may be used with a bone anchoring device different than the ones described above. The specific shape of the first and second tube and/or the inner and outer tube may vary. In particular, the receiving part may be configured for inserting the bone anchoring element from above, i.e., the receiving part may be a top loader instead of the bottom loader described above. As another possible modification, the receiving part may be configured such that the head and the rod are fixed simultaneously by advancing the fixation element 35 in the coaxial bore 40 between the legs. Furthermore, the present disclosure is not limited to an instrument for use with a polyaxial bone anchoring device but may also be used with a monoaxial bone anchoring device. In general, the instrument described above may be used with any receiving part that has a recess defining two legs.

Furthermore, the present disclosure is not limited to the use of the instrument for advancing the fixation element 35 within the receiving part. Rather, the screw driver may also engage another screw member provided within the receiving part or the recess in the head of the bone anchoring element.

Although connection of the grip member 3 and the tube member 2 is implemented by a polygonal through-hole 12a and the polygonal engagement section 19 described above, it should be understood that any other suitable connection can be applied that prevents rotation of the grip member 3 around the longitudinal axis I while at the same time providing access to the internal channel 17. Alternatively, the grip member 3 and the tube member 2 can also be provided integrally, i.e., as a single part, or can be otherwise firmly attached to one another.

In the above embodiments, the first and second tubes have a substantially cylindrical shape with a substantially circular cross-section. It should be understood that the shape of the first and/or second tube and/or the internal channel of the second tube may have any other shape or cross-section. For example, the inner channels of the second tube may have a polygonal, such as a hexagonal, cross-section at least in a section thereof, and the first tube may have a correspondingly shaped polygonal, e.g. hexagonal, outer surface at least in a section thereof.

The instrument 1, 1' and the bone anchoring device 10, 10' may be provided as separate parts, or may in some cases be provided together as a system including both the bone anchoring device 10, 10' and the instrument 1, 1'.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument for use with a receiving part for connecting a bone anchoring element to a rod, the receiving part comprising two legs that define a recess for receiving the rod, the instrument comprising:
   a tube having a first end, a second end, and a longitudinal axis that extends between the first end and the second end, and defining a coaxial internal channel that opens towards the first end and the second end; and
   two protruding portions monolithically formed with the tube and positioned diametrically opposite to one another for engagement with the recess of the receiving part to prevent rotational movement of the tube relative to the receiving part, wherein the tube comprises two diametrically opposite intermediate portions at the first end that are positioned circumferentially between the protruding portions in a manner such that the first end of the tube forms a closed ring;
   wherein an outer diameter of the first end of the tube at the intermediate portions measured along a first direction that intersects the longitudinal axis is less than an outer diameter of another region of the tube adjacent where the protruding portions connect measured along a direction that intersects the longitudinal axis and that is parallel to the first direction, to facilitate positioning of the intermediate portions in a coaxial central passage of the receiving part when the protruding portions are advanced into the recess of the receiving part;
   wherein each of the protruding portions has a first region that extends radially outwardly from an outer surface of the tube at the first end and a second region that extends axially away from the first end in a direction opposite the second end, and wherein an axial length of each of the protruding portions is less than an axial length of a region of the tube between the protruding portions and the second end of the tube.

2. The instrument of claim 1, wherein each of the protruding portions has an end face with a cylindrical recess having a diameter that substantially corresponds to a diameter of the rod.

3. The instrument of claim 1, further comprising an inner shaft with a drive portion at one end, the inner shaft being movable axially in the internal channel of the tube.

4. The instrument of claim 3, wherein the internal channel and the inner shaft each comprises a substantially cylindrically shaped portion.

5. The instrument of claim 1, wherein the tube is a first tube, and the instrument further comprises a second tube positioned at least partially around the first tube.

6. The instrument of claim 5, wherein the second tube extends around an outside of each of the protruding portions.

7. The instrument of claim 5, wherein the first tube and second tube are formed monolithically with one another.

8. The instrument of claim 5, wherein the first tube and the second tube are separable from one another.

9. The instrument of claim 1, further comprising a grip portion for holding the tube.

10. The instrument of claim 1, wherein an axial length of the entire tube is greater than the axial length of each of the protruding portions.

11. A system comprising:
   a receiving part for connecting a bone anchoring element to a rod, the receiving part comprising two legs that define a recess for receiving the rod; and
   an instrument for use with the receiving part, the instrument comprising a tube having a first end, a second end, and a longitudinal axis that extends between the first end and the second end, and defining a coaxial internal channel that opens towards the first end and the second end, and two protruding portions monolithically formed with the tube and positioned diametrically opposite to one another, the tube further comprising two diametrically opposite intermediate portions at the first end that are positioned circumferentially between the protruding portions in a manner such that the first end of the tube forms a closed ring;
   wherein the protruding portions are configured to engage and extend at least partially into the recess of the receiving part when the instrument is attached to the receiving part to prevent rotational movement of the tube relative to the receiving part, while the intermediate portions are configured to be positioned in a coaxial central passage of the receiving part; and
   wherein each of the protruding portions has a first region that extends radially outwardly from an outer surface of the tube at the first end and a second region that extends axially away from the first end in a direction opposite the second end, and wherein an axial length of each of the protruding portions is less than an axial length of a region of the tube between the protruding portions and the second end of the tube.

12. The system of claim 11, wherein the legs of the receiving part each comprises an inner thread, and wherein the instrument further comprises an inner shaft that is movable axially in the internal channel of the tube to advance a fixation element having an outer thread corresponding to the inner thread of the legs into the recess of the receiving part.

13. The system of claim 11, wherein an axial length of each of the protruding portions corresponds substantially to an axial distance between a free end of the legs of the receiving part and a rod that is fully inserted into the recess of the receiving part.

14. The system of claim 11, wherein a width of each of the protruding portions in a circumferential direction of the tube is substantially equal to or slightly smaller than a width of the recess of the receiving part.

15. The system of claim 11, wherein a thickness of each of the protruding portions in a radial direction corresponds substantially to a thickness of the legs of the receiving part in the radial direction.

16. The system of claim 11, wherein an outer diameter of the first end of the tube measured at the intermediate portions is less than an outer diameter of another region of the tube adjacent where the protruding portions connect.

17. The system of claim 11, wherein the tube is a first tube, and the instrument further comprises a second tube positioned at least partially around the first tube and configured to extend around an outside of the receiving part when the instrument is attached to the receiving part.

18. The system of claim 11, further comprising:
the bone anchoring element comprising a shank and a head that defines a tool recess for a driving tool for driving the shank into bone;
wherein the internal channel of the tube of the instrument is sized to accommodate the driving tool therethrough to engage the tool recess on the head when the bone anchoring element is assembled to the receiving part and the instrument is attached to the receiving part.

19. A method for coupling a rod to a bone with a bone anchoring device comprising a bone anchoring element, a receiving part connected to the bone anchoring element and comprising two legs that define a recess for receiving the rod, and a fixation element, and using an instrument comprising a tube having a first end, a second end, and a longitudinal axis that extends between the first end and the second end, and defining a coaxial internal channel that opens towards the first end and the second end, and two protruding portions monolithically formed with the tube and positioned diametrically opposite to one another, the tube further comprising two diametrically opposite intermediate portions at the first end that are positioned circumferentially between the protruding portions in a manner such that the first end of the tube forms a closed ring, wherein each of the protruding portions has a first region that extends radially outwardly from an outer surface of the tube at the first end and a second region that extends axially away from the first end in a direction opposite the second end, and wherein an axial length of each of the protruding portions is less than an axial length of a region of the tube between the protruding portions and the second end of the tube, the method comprising:
anchoring the bone anchoring element to bone;
inserting the rod in the recess;
attaching the instrument to the receiving part such that the protruding portions engage and extend at least partially into the recess of the receiving part to prevent rotational movement of the tube relative to the receiving part, while the intermediate portions are positioned in a coaxial central passage of the receiving part; and
using the instrument to advance the fixation element into the recess to lock the rod relative to the receiving part.

20. An instrument for use with a receiving part for connecting a bone anchoring element to a rod, the receiving part comprising two legs that define a recess for receiving the rod, the instrument comprising:
a first tube having a first end, a second end, and a longitudinal axis that extends between the first end and the second end, and defining a coaxial internal channel that opens towards the first end and the second end;
at least one protruding portion monolithically formed with the first tube that is engageable with the recess of the receiving part to prevent rotational movement of the first tube relative to the receiving part; and
a second tube positioned around at least the first end of the first tube;
wherein the first end of the first tube and a portion of the second tube that extends around the first end of the first tube both form a closed ring, wherein the at least one protruding portion has a first region that extends radially outwardly from an outer surface of the first tube at the first end and a second region that extends axially away from the first end in a direction opposite the second end, and wherein an axial length of the at least one protruding portion is less than an axial length of a region of the first tube between the at least one protruding portion and the second end of the first tube.

* * * * *

UNITED STATES PATENT AND TRADEMARK OFFICE
CERTIFICATE OF CORRECTION

| | | |
|---|---|---|
| PATENT NO. | : 12,114,902 B2 | Page 1 of 1 |
| APPLICATION NO. | : 17/124975 | |
| DATED | : October 15, 2024 | |
| INVENTOR(S) | : Timo Biedermann et al. | |

It is certified that error appears in the above-identified patent and that said Letters Patent is hereby corrected as shown below:

In the Specification

In Column 5, Line 17, delete "dl" and insert -- d1 --.

Signed and Sealed this
Eleventh Day of February, 2025

Coke Morgan Stewart
*Acting Director of the United States Patent and Trademark Office*